United States Patent [19]
Jacobs

[11] Patent Number: 5,334,765
[45] Date of Patent: Aug. 2, 1994

[54] CARBAMOYL DERIVATIVES

[75] Inventor: Robert T. Jacobs, Wilmington, Del.

[73] Assignee: Imperial Chemical Industries PLC, London, England

[21] Appl. No.: 137,245

[22] Filed: Oct. 14, 1993

Related U.S. Application Data

[60] Division of Ser. No. 927,762, Aug. 10, 1992, Pat. No. 5,286,740, which is a continuation of Ser. No. 626,072, Dec. 11, 1990, abandoned.

[30] Foreign Application Priority Data

Dec. 11, 1989 [GB] United Kingdom ............... 8927981

[51] Int. Cl.$^5$ ........................................... C07C 211/03
[52] U.S. Cl. ........................................... 564/510
[58] Field of Search ........................................... 564/510

[56] References Cited

U.S. PATENT DOCUMENTS 4,918,094  4/1990  Bernstein et al. ................... 514/419

FOREIGN PATENT DOCUMENTS 114950  8/1984  European Pat. Off. ............ 514/419

OTHER PUBLICATIONS

Chem. Ber. 119, 2233–2248, Gassen et al., 1986.
CA 115 (17): 183090g Preparation of . . . antagonists, Jacobs, pp. 903–904, 1991.
CA 117(15):150542b (2R)–methyl–4,4,4-trifluorobutylamine Jacobs et al., p. 784, 1992.
CA 117(15):150884q 3-Alkylated indoles Jacobs et al., p. 816, 1992.

Primary Examiner—Mary C. Lee
Assistant Examiner—Joseph K. McKane
Attorney, Agent, or Firm—Thomas F. Jackson

[57] ABSTRACT

The present invention concerns novel carbamoyl derivatives of formula I, set out herein, which antagonize the pharmacological actions of one or more of the arachidonic acid metabolites known as leukotrienes, making them useful whenever such antagonism is desired, such as in the treatment of those diseases in which leukotrienes are implicated, for example, in the treatment of allergic or inflammatory diseases, or of endotoxic or traumatic shock conditions. The invention also provides pharmaceutical compositions containing the novel derivatives for use in such treatments, methods for their use and processes and intermediates for the manufacture of the novel derivatives.

2 Claims, No Drawings

CARBAMOYL DERIVATIVES

This is a divisional of co-pending application Ser. No. 07/927,762 filed on 10 Aug. 1992, now U.S. Pat. No. 5,286,740, which application is a continuation of the application Ser. No. 07/626,072 filed on 11 Dec. 1990 and now abandoned.

This invention concerns a novel carbamoyl derivatives, and, more particularly, a novel 5-(2-methyl-4,4,4-trifluorobutylcarbamoyl)indole derivatives which antagonize the pharmacological actions of one or more of the arachidonic acid metabolites known as leukotrienes (hereafter referred to as "leukotriene antagonist properties"). The novel derivatives are useful whenever such antagonism is desired. Thus, such compounds may be of value in the treatment of those diseases in which leukotrienes are implicated, for example, in the treatment of allergic or inflammatory diseases, or of endotoxic or traumatic shock conditions. The invention also provides pharmaceutical compositions containing the novel derivatives for use in such treatments, methods for their use and processes and intermediates for the manufacture of the novel derivatives.

In European Patent Application publication number 220,066 there is disclosed a series of carbamoyl heterocycles which includes 5-carbamoylindole derivatives of formula Ia (formula set out hereinbelow following the Examples, together with other formulae denoted by Roman numerals) wherein, inter alia, $R^1$ includes (2-10C)alkyl optionally containing 1 or more fluorine substituents, Ra is hydrogen or methyl, Rc is hydrogen or (1-4C)alkoxy, Rd includes hydrogen and (1-10C)alkyl, and M includes a residue of formula —CO.NH.SO$_2$R$^6$ in which the values of $R^6$ include (6-12C)aryl which may bear 1 or 2 substituents selected from a group consisting of halogeno, amino, (1-4C)alkyl, (1-4C)alkoxy and trifluoromethyl, and the pharmaceutically acceptable salts thereof. It has now been discovered, and herein lies the basis of the claimed invention, that particularly useful leukotriene antagonist properties are shown by novel carbamoyl derivates of formula Ia in which $R^1$ is 2-methyl-4,4,4-trifluorobutyl, and the other groups have specified values, as defined below.

According to the invention there is provided a 5-(2-methyl-4,4,4-trifluorobutylcarbamoyl)indole derivative of formula I both in racemic form and in the form of a substantially pure enantiomer, particularly the (R.)-form; or a pharmaceutically acceptable salt thereof.

It will be appreciated that, owing to the asymmetrically substituted carbon atom in the 2-methyl-4,4,4-trifluorobutylcarbamoyl group, the compound of formula I may exist in, and be isolated in, optically-active and racemic forms. The compound may exhibit polymorphism. The compound may form solvates. It is to be understood that the present invention encompasses any racemic, optically-active or polymorphic form, or solvate, or mixtures thereof, which form possesses leukotriene antagonist properties, it being well known in the art how to prepare optically-active forms (for example, by resolution of the racemic form or by synthesis from optically-active starting materials) and how to determine the leukotriene antagonist properties by the standard tests described hereinafter. It may be preferred to use the compound of formula I in a form which is characterized as containing, for example, at least 95%, 98% or 99% enantiomeric excess (ee) of the (R.)-form.

It is preferred that the 2-methyl-4,4,4-trifluorobutyl carbamoyl group be of the optically active (R.)-form.

Specific forms of the compound of the invention are described in the accompanying examples and may be used either in the free acid form or as a corresponding pharmaceutically acceptable salt.

Examples of suitable pharmaceutically acceptable salts are salts formed with bases which form a physiologically acceptable cation, such as alkali metal (especially lithium, sodium and potassium), alkaline earth metal (especially calcium and magnesium), aluminum and ammonium salts, as well as salts made with appropriate organic bases such as triethylamine, morpholine, piperidine and triethanolamine.

A compound of formula I may be made by processes which include processes well known in the chemical art for the production of structurally analogous carbocyclic compounds. Such processes for the manufacture of a compound of formula I as defined above are provided as further features of the invention and are illustrated by the following procedures in which the meanings of generic radicals are as defined:

(A) Reacting a corresponding compound of formula II wherein T is carboxy (which compound is hereinafter referred to as "benzoic acid of formula II") with 2-methylbenzenesulfonamide in the presence of a dehydrating agent or reacting a reactive derivative of a benzoic acid of formula II with 2-methylbenzenesulfonamide, or a salt thereof.

Thus, for example, a free benzoic acid of formula II may be reacted with a suitable dehydrating agent, for example, with dicyclohexylcarbodiimide or 1-(3-dimethylaminopropyl)-3-ethylcarbodiimide, or with a hydrochloride or hydrobromide salt thereof, optionally together with an organic base, for example, 4-dimethylaminopyridine, and with 2-methylbenzenesulfonamide in the presence of a suitable solvent or diluent, for example, methylene chloride, at a temperature in the range of, for example, 10° to 50° C., but preferably at or near ambient temperature.

Alternatively, a reactive derivative of a benzoic acid of formula II, for example, an acid halide (such as the acid chloride), acid anhydride or a mixed acid anhydride (such as that formed from N,N-diphenylcarbamic acid and the benzoic acid of formula II by reaction of the sodium salt of the latter acid with N,N-diphenylcarbamoylpyridinium chloride), may be reacted with an alkali metal salt (such as the lithium, sodium or potassium salt) of 2-methylbenzenesulfonamide, conveniently at or near ambient temperature and in a suitable solvent or diluent, for example, tetrahydrofuran, dimethylformamide or methylene chloride.

A benzoic acid of formula II wherein T is a carboxy group may be obtained by decomposing a suitable benzoic ester of formula II in which T is COOR$^h$ wherein R$^h$ is a conveniently removed acid protecting group (which compound is hereinafter referred to as "benzoic ester of formula II"), for example, phenyl, benzyl, or (1-6C)alkyl optionally bearing an acetoxy, (1-4C)alkoxy or (1-4C)alkylthio substituent. A particular value for R$^h$ is, for example, methyl, ethyl, propyl, t-butyl, acetoxymethyl, methoxymethyl, 2-methoxyethyl, methylthiomethyl, phenyl, or benzyl. A preferred value for R$^h$ is methyl.

It will be appreciated that the decomposition of a benzoic ester of formula II can be performed using any one of a variety of procedures well known in the art of organic chemistry. A preferred method for decomposing an ester of formula II comprises reacting the ester with a suitable base, for example, as described in Example 1.f. When such a method is employed, the resulting benzoic acid of formula II, wherein T is a carboxy group, is initially obtained as the corresponding salt of the base used for the hydrolysis and may be isolated as such or converted to the free acid form by a conventional acidification procedure, for example, by reaction with a suitable strong acid such as hydrochloric or sulfuric acid.

(B) Acylating 2-methyl-4,4,4-trifluorobutylamine with a carboxylic acid of formula III wherein U is carboxy (which compound is hereinafter referred to as "indole carboxylic acid of formula III") in the presence of a dehydrating agent or with a reactive derivative of an indole carboxylic acid of formula III. It will be clear to one skilled in the art that use of racemic 2-methyl-4,4,4-trifluorobutylamine will afford a racemic carbamoyl derivative of formula I and that use of 2-methyl-4,4,4-trifluorobutylamine which is substantially enantiomerically pure will afford a corresponding carbamoyl derivative of formula I which is substantially enantiomerically pure.

Thus, for example, an indole carboxylic acid of formula III may be reacted with a suitable dehydrating agent, for example, with 1-(3-dimethylaminopropyl)-3-ethyl carbodiimide, or with a hydrochloride or hydrobromide salt thereof, optionally together with an organic base, for example, 4-dimethylaminopyridine, and with 2-methyl-4,4,4-trifluorobutylamine, or with a salt thereof, especially a hydrochloride or hydrobromide salt, optionally together with an organic base, for example, 4-dimethylaminopyridine, in the presence of a suitable solvent or diluent, for example tetrahydrofuran or 1,2-dimethoxyethane, at a temperature in the range of, for example 10° to 85° C., for example in tetrahydrofuran at or near 67° C.

Alternatively, a reactive derivative of an indole acid of formula III, for example, an acid halide (such as the acid chloride), acid anhydride or mixed acid anhydride (such as that formed with ethyl chloroformate in the presence of an organic base such as, for example triethylamine or 4-dimethylamimopyridine) or a lower alkyl ester (such as the methyl ester) may be used as the acylating agent, conveniently together with a suitable inert solvent or diluent, for example dichloromethane, tetrahydrofuran or 1,2-dimethoxyethane.

An indole carboxylic acid of formula III wherein U is a carboxy group may be obtained by decomposing a suitable indole ester of formula III in which U is $COOR^j$ wherein $R^j$ is a conveniently removed acid protecting group (which compound is hereinafter referred to as "indole ester of formula III"), for example, phenyl, benzyl, or (1-6C)alkyl optionally bearing an acetoxy, (1-4C)alkoxy or (1-4C)alkylthio substituent. A particular value for $R^j$ is, for example, methyl, ethyl, propyl, t-butyl, acetoxymethyl, methoxymethyl, 2-methoxyethyl, methylthiomethyl, phenyl, or benzyl. Preferred values for $R^j$ include methyl and benzyl.

It will be appreciated that the decomposition of an indole ester of formula III can be performed using any one of a variety of procedures well known in the art of organic chemistry. A preferred method for decomposing an indole ester of formula III comprises reacting the ester with a suitable base, for example, as described in Example 3.c and Example 3.l. When such a method is employed, the resulting indole carboxylic acid of formula III, wherein U is a carboxy group, is initially obtained as the corresponding salt of the base used for the hydrolysis and may be isolated as such or converted to the free acid form by a conventional acidification procedure, for example, by reaction with a suitable strong acid such as hydrochloric or sulfuric acid.

The novel 2-methyl-4,4,4-trifluorobutylamine, both in racemic form and in the form of a substantially pure enantiomer, particularly the (R)-form, (preferably isolated as an acid addition salt, for example the hydrochloride), and its preparation provide further aspects of the invention based upon the utility as a chemical intermediate. The novel amine may be prepared in racemic or optically active form from 4,4,4-trifluorobutyric acid or an ester thereof, for example the ethyl ester, as described in the Examples. Thus, in Example 1, parts g.-j. and parts k.-u., two similar procedures for preparation of racemic 2-methyl-4,4,4-trifluorobutylamine hydrochoride are described. Preparation of the optically active (R)-2-methyl-4,4,4-trifluorobutylamine, isolated as the hydrochloride salt, using the chiral auxiliary reagent (4R,5S)-(+)-4-methyl-5-phenyl-2-oxazolidinone, is described in Example 2, parts a.-g.; an alternative preparation is described in Example 3, parts m.-s.

If a compound of formula I in substantially enantiomerically pure form is required, it may be obtained by a procedure using enantiomerically pure starting materials, as described above, or by separation of the desired optically active form using a conventional method. If a compound of formula I is obtained and a pharmaceutically acceptable salt thereof is required, the pharmaceutically acceptable salt may be obtained by reacting the compound of formula I with a suitable base which affords a physiologically acceptable cation.

The necessary starting materials for the above procedures may be made by procedures which are selected from standard techniques of organic chemistry, techniques which are analogous to the synthesis of known, structurally similar compounds, and techniques which are analogous to the above described methods and those described in the Examples.

The starting materials of formulae II and III conveniently may be prepared beginning with indole-5-carboxylic acid (formula IV wherein U is carboxy). Thus, the acid of formula IV wherein U is carboxy may be esterified by a conventional method to form a corresponding ester of formula IV wherein U has the value $COOR^j$ and $R^j$ is defined as above. An ester of formula IV wherein U is $COOR^j$ may be substituted at the 3-position of the indole using an α-bromo toluic ester of formula V wherein T is $COOR^h$ and $R^h$ has the values defined above, using a similar method to that described in Example 1.b. to provide a corresponding diester of formula VI wherein T is $COOR^h$ and U is $COOR^j$. An alternative preparation of a diester of formula VI is described in Example 3, parts d.-g. An α-bromo toluic ester of formula V may be prepared by a conventional method, for example as described in European Patent Application publication number 220,066 or in U.S. Pat. No. 4,859,692. A diester of formula VI may be converted into a corresponding diester of formula VII by alkylation at the 1-position of the indole using a similiar procedure to that described in Example 1.c. or Example 3.h. and a conventional alkylating agent, for example methyl iodide.

By selective conversion of the ester group of formula $COOR^j$ into a carboxy group, a diester of formula VII wherein T is $COOR^h$ and U is $COOR^j$ may be converted into a corresponding indole carboxylic acid of formula VII wherein T is COOR$^h$ and U is carboxy. For example, a diester of formula VII wherein T is COOR$^h$ in which R$^h$ is methyl and U is COOR$^j$ in which R$^j$ is benzyl may be converted into a corresponding indole carboxylic acid of formula VII wherein U is carboxy and T is COOR$^h$ in which R$^h$ is methyl by hydrogenolysis of the benzyl group using a similar method to that described in Example 1.d. The resulting indole carboxylic acid of formula VII may be converted into a corresponding starting material benzoic ester of formula II wherein T is COOR$^h$ using a similiar procedure to that of (B) above, for example as described in Example 1.e. and Example 2.h. Clearly, use of racemic 2-methyl-4,4,4-trifluorobutylamine will afford racemic benzoic ester of formula II and use of substantially enantiomerically pure amine will afford substantially enantiomerically pure benzoic ester of formula II.

Alternatively, by selective conversion of the ester group of formula COOR$^h$ into a carboxy group, a diester of formula VII wherein T is COOR$^h$ and U is COOR$^j$ may be converted into a corresponding benzoic acid of formula VII wherein T is carboxy and U is COOR$^j$. For example a dimethyl ester of formula VII wherein T is COOR$^h$ and U is COOR$^j$ in which both R$^h$ and R$^j$ are methyl may be hydrolyzed selectively by a similar method to that described in Example 3.a. and Example 3.i. to afford a benzoic acid of formula VII wherein T is carboxy and U is COOR$^j$ in which R$^j$ is methyl. The resulting benzoic acid of formula VII may be converted into a starting material indole ester of formula III wherein U is COOR$^j$ using a similar procedure to (A) above, for example as described in Example 3.b. and Example 3, parts j.-k.

The starting materials of formula II wherein T is carboxy or COOR$^h$, both in racemic form and in substantially enantiomerically pure form, are novel and are provided as further features of the invention based upon their utility as chemical intermediates. When a starting material of formula II which is substantially enantiomerically pure is required, it will be clear to one skilled in the art that the starting material may be prepared using substantially enantiomerically pure 2-methyl-4,4,4-trifluorobutylamine or that the racemic starting material may be resolved by a conventional method.

As stated previously, the compound of formula I possesses leukotriene antagonist properties. Thus, it antagonises at least one of the actions of one or more of the arachidonic acid metabolites known as leukotrienes, for example, C$_4$, D$_4$, and/or E$_4$, which are known to be powerful spasmogens (particularly in the lung), to increase vascular permeability and to be implicated in the pathogenesis of asthma and inflammation, as well as of endotoxic shock and traumatic shock. The compound of formula I is thus useful in treatment of diseases in which leukotrienes are implicated and in which antagonism of their action is desired. Such diseases include, for example, allergic pulmonary disorders such as asthma, hay fever and allergic rhinitis and certain inflammatory diseases such as bronchitis, ectopic and atopic eczema, and psoriasis, as well as vasospastic cardiovascular disease, and endotoxic and traumatic shock conditions.

The compound of formula I is a potent leukotriene antagonist and is useful whenever such activity is desired. For example, the compound of formula I is of value as a pharmacological standard for the development and standardization of new disease models and assays for use in developing new therapeutic agents for treating the diseases in which the leukotrienes are implicated.

When used in the treatment of one or more of the above mentioned diseases, the compound of formula I is generally administered as an appropriate pharmaceutical composition which comprises the compound of formula I as defined hereinbefore together with a pharmaceutically acceptable diluent or carrier, the composition being adapted for the particular route of administration chosen. Such compositions are provided as a further feature of the invention. They may be obtained employing conventional procedures and excipients and binders and may be in a variety of dosage forms. For example, they may be in the form of tablets, capsules, solutions or suspensions for oral administration; in the form of suppositories for rectal administration; in the form of sterile solutions or suspensions for administration by intravenous or intramuscular injection or infusion; in the form of aerosols or nebuliser solutions or suspensions for administration by inhalation; and in the form of powders together with pharmaceutically acceptable inert solid diluents such as lactose for administration by insufflation. If a solid form of a compound of formula I is required, it may be preferred to use an amorphous form, which amorphous form may be prepared by adding an aqueous acid, for example hydrochloric acid, to a solution of the sodium salt of the compound of formula I in an alcohol-water mixture, for example methanol-water mixture, to precipitate the compound of formula I.

For oral administration a tablet or capsule containing up to 250 mg (and typically 5 to 100 mg) of the compound of formula I may conveniently be used. Similarly, for intravenous or intramuscular injection or infusion a sterile solution or suspension containing up to 10% w/w (and typically 0.05 to 5% w/w) of the compound of formula I may conveniently be used.

The dose of the compound of formula I to be administered will necessarily be varied according to principles well known in the art taking account of the route of administration and the severity of the condition and the size and age of the patient under treatment. However, in general, the compound of formula I will be administered to a warm-blooded animal (such as man) so that a dose in the range of, for example, 0.01 to 25 mg/kg (and usually 0.1 to 5 mg/kg) is received.

The leukotriene antagonist properties of the compound of formula I may be demonstrated using standard tests. Thus, for example, they may be demonstrated *in vitro* using the standard guinea-pig tracheal strip preparation described by Krell (*J. Pharmacol. Exp. Ther.*, 1979, 211, 436) and as also described in European Patent Application publication number 220,066 and in U.S. Pat. No. 4,859,692.

The selectivity of action of compounds as leukotriene antagonists as opposed to non-specific smooth muscle depressants may be shown by carrying out the above *in vitro* procedure using the non-specific spasmogen barium chloride at a concentration of $1.5 \times 10^{-3}$M, again in the presence of indomethacin at $5 \times 10^{-6}$M.

Alternatively, the antagonistic properties of the compound of formula I can be demonstrated *in vitro* by a receptor-ligand binding assay described by Aharony (*Fed. Proc.*, 1987, 46, 691). According to this procedure, membrane fractions, containing the LTD$_4$/E$_4$ receptors, are prepared from guinea-pig lung parenchyma and incubated for 30 minutes at 22° C. with 1 nM $^3$H-LTD$_4$ in the absence or presence of tested antagonist.

Specific binding, determined under conditions that prevent enzymatic metabolism of $^3$H-LTD$_4$, is the net result of total $^3$H-LTD$_4$ binding minus nonspecific binding determined in the presence of 1-2000 fold excess unlabelled LTD$_4$. Each assay is done in duplicate and results (Ki values) are typically a mean of several such determinations in individual receptor batches.

The % inhibition by a tested antagonist, relative to control binding (vehicle alone), is expressed as a fraction of log[antagonist] concentration (in molar units) and the half-maximal inhibition (IC$_{50}$) determined by computerized non-linear least-square analysis. The binding constant (Ki) is then calculated from IC$_{50}$ by the Cheng-Prusoff equation:

$$Ki = \frac{IC_{50}}{\left[1 + \frac{[L]}{Kd}\right]}$$

where [L] is $^3$H-LTD$_4$ concentration and Kd is the affinity constant of LTD$_4$ to this receptor, determined separately for each batch. (*Biochem. Pharmacol.*, 1973, 22, 3099-3108).

In general, the compounds of formula I tested demonstrated statistically significant activity as LTC$_4$, LTD$_4$ and/or LTE$_4$ antagonists in one of the above tests at a concentration of about $10^{-8}$M or much less. For example, a pKi value of 9.4 was typically determined for the compound of Example 2.

Activity as a leukotriene antagonist may also be demonstrated in vivo in laboratory animals, for example, in a routine guinea-pig aerosol test described by Snyder, et al. (*J. Pharmacol. Methods*, 1988, 19, 219). In this test the particularly useful leukotriene antagonist properties of the carbamoyl derivative of formula I may be demonstrated. According to this procedure, guinea-pigs are pre-dosed with test compound as a solution in poly-(ethylene glycol) (generally 1 hour) before an aerosol challenge of leukotriene LTD$_4$ (starting with 2 ml of a 30 microgram/ml solution) and the effect of the test compound on the average time of leukotriene initiated change in breathing pattern (such as onset of dyspnea) recorded and compared with that in undosed, control guinea-pigs. Percent protection engendered by a test compound was calculated from the time delay to the onset of dyspnea compared to that for control animals. Typically, an ED$_{50}$ of 1.1 μmol/kg for the compound of Example 2 following oral administration was determined, without any indication of untoward side-effects at several multiples of the minimum effective dose. By way of comparison, an oral ED$_{50}$ of 19.2 μmol/kg was measured for the compound of formula Ia wherein R$^1$ is cyclopentylmethyl, Ra is hydrogen, Rd is methyl, Rc is methoxy, and M is a residue of formula —CO.NH.SO$_2$R$^6$ in which R$^6$ is 2-methylphenyl (Example 10 of European Patent Application publication number 220,066).

The invention will now be illustrated by the following non-limiting examples in which, generally, unless stated otherwise:

(i) temperatures are given in degrees Celsius (°C.); operations were carried out at room or ambient temperature, that is, at a temperature in the range of 18°-25° C.; air or moisture sensitive reactions were performed under an inert (argon or nitrogen) atmosphere;

(ii) evaporation of solvent was carried out using a rotary evaporator under reduced pressure (600-4000 pascals; 4.5-30 Am Hg) with a bath temperature of up to 60° C.;

(iii) flash chromatography was carried out on Merck Kieselgel (Art 9385) and column chromatography on Merck Kieselgel 60 (Art 7734); [these materials were obtained from E. Merck, Darmstadt, W. Germany]; thin layer chromatography (TLC) was carried out on Artaltech 0.25 mm silica gel GHLF plates (Art 21521), obtainable from Analtech, Newark, Del., USA; gas-liquid chromatography (GLC) was carried out on a 0.2 mm×25 m fused silica glass capillary column with 5% phenyl methyl silicone as the stationary phase, with a flow rate of 0.7 mL/min and an oven temperature program of 50° C. for 5 min, then 10° C./min increase to 275° C.; the injector temperature was 225° C. and detector 275° C.; retention times (t$_R$) are given in min;

(iv) in general, the course of reactions was followed by TLC and reaction times are given for illustration only;

(v) melting points are uncorrected and (d) indicates decomposition; the melting points given are those obtained for the materials prepared as described; polymorphism may result in isolation of materials with different melting points in some preparations;

(vi) all final products were essentially pure by TLC and had satisfactory nuclear magnetic resonance (NMR) spectra and microanalytical data;

(vii) yields are given for illustration only;

(viii) when given, NMR data is in the form of delta values for major diagnostic protons, given in parts per million (ppm) relative to tetramethylsilane (TMS) as an internal standard, determined at 80 MHz, 250 MHz, 300 MHz or 400 MHz using CDCl$_3$, DMSO-d$_6$ or CD$_3$OD as solvent; conventional abbreviations for signal shape are used, for example: s, singlet; d, doublet; m, multiplet; br, broad; etc.; the "observed" (rather than calculated) shifts for complex signals are reported; in addition "Ar" signifies an aromatic group or signal; measurements of enantiomeric excess (ee) were made by $^{19}$F NMR using the chiral shift reagent, 2,2,2-trifluoro-1-(9-anthryl)ethanol-d$_{11}$ (TFAE-d$_{11}$); the fluorine resonance for a compound of formula I dissolved in CDCl$_3$ which appears at about $-63.8$ ppm from CFCl$_3$ when measured at 376.5 MHz demonstrates a greater shift of the signal for the (R)-isomer than for the signal of the (S)-isomer in the presence of added (R)-(−)-TFAE-d$_{11}$;

(ix) reduced pressures are given as absolute pressures in pascals (Pa); other pressures are given as gauge pressures in bars;

(x) chemical symbols have their usual meanings; in general the symbols for units of the SI system or those accepted for use with the SI system are used (e.g., L, mL, g, mg, h, min); the following abbreviations have also been used: v (volume), w (weight), mp (melting point), bp (boiling point);

(xi) solvent ratios are given in volume: volume (v/v) terms; and (xii) mass spectra (MS) were run with an electron energy of 70 electron volts in the chemical ionization (CI) mode or electron impact (EI) mode; generally only the peak attributable to the parent ion is reported.

EXAMPLE 1

3-Methoxy-4-[1-methyl-5-(2-methyl-4,4,4-trifluorobutylcarbamoyl)indol-3-ylmethyl]-N-(2-methylphenylsulfonyl)benzamide A solution of 3-methoxy-4-[1-methyl-5-(2-methyl-4,4,4-trifluorobutylcarbamoyl)indol-3-ylmethyl]benzoic acid (250 mg), 4-dimethylaminopyridine (69.8 mg), 1-(3-dimethylaminopropyl)-3-ethylcarbodiimide hydrochloride (127 mg) and 2-methylbenzenesulfonamide (95.4 mg) in methylene chloride (5 mL) was stirred under a nitrogen atmosphere for 24 hours. The mixture was diluted with methylene chloride, washed (10% (w/v) hydrochloric acid, water), and evaporated. The resulting rose-colored foam was dissolved in methylene chloride (5 mL), filtered through a 0.45 micron membrane filter, and precipitated by addition to hexane (50 mL). The solid was collected by filtration to give the title compound (189.2 mg, 57%) as a pale pink powder; mp 147°–149 °C.

Analysis for $C_{31}H_{32}F_3N_3O_5S$: Calculated: C, 60.48; H, 5.24; N, 6.83 Found: C, 60.39; H, 5.60; N, 6.59

The starting benzoic acid was prepared as follows:

a. Benzyl indole-5-carboxylate.

A solution of indole-5-carboxylic acid (68.3 g), benzyl alcohol (64.9 g) and triphenylphosphine (157.0 g) in tetrahydrofuran (1.2 L) was cooled to 5° C. and treated dropwise with diethyl azodicarboxylate (90.0 g). Upon completion of the addition, the mixture was allowed to warm to room temperature. The reaction was stirred for 24 hours and then evaporated. The residue was taken up in diethyl ether (1 L) and filtered. The filtrate was evaporated to give a yellow syrup which was purified by flash chromatography, eluting sequentially with 2:1, 1:1 and 1:2 hexane:methylene chloride, to afford a yellow-white solid. This material was triturated with 1:1 hexane: methylene chloride (300 mL) and filtered to give benzyl indole-5-carboxylate as a white solid (74.2 g, 70%); mp 127°–129 °C.; partial NMR (300 MHz, $CDCl_3$): 5.39 (s, 2H, $CH_2$), 6.61 (m, 1H, indole-H(2)), 8.56 (br, 1H, NH).

b. Methyl 4-(5-benzyloxycarbonylindol-3-ylmethyl)-3-methoxybenzoate

A solution of benzyl indole-5-carboxylate (86.8 g), methyl 4-bromomethyl-3-methoxybenzoate (89.5 g) and potassium iodide (57.4 g) in N,N-dimethylformamide (900 mL) was heated to 80° C. for 10 hours. The reaction mixture was evaporated and partitioned between diethyl ether and water. The organic layer was separated and washed with water. The aqueous washes were combined and extracted with diethyl ether. The combined organic extract was dried ($MgSO_4$) and evaporated. The residue was purified by flash chromatography, eluting sequentially with 0:1:1, 2:48:50, 4:46:50, 5:45:50, and 10:40:50 ethyl acetate:hexane:methylene chloride, to afford methyl 4-iodomethyl-3-methoxybenzoate (27.8 g), recovered benzyl indole-5-carboxylate (29.6 g), and the crude product as a tan solid (50.6 g). Treatment of the recovered benzyl indole-5-carboxylate (29.6 g) in N,N-dimethylformamide (250 mL) with methyl 4-iodomethyl-3-metboxybenzoate (29.8 g) at 80° C. for 12 hours, followed by evaporation, gave a dark residue, which was dissolved in diethyl ether and washed with water (3 times). The aqueous washes were combined and extracted with diethyl ether. The combined organic extract was dried ($MgSO_4$) and evaporated. The residue was purified by flash chromatography, eluting sequentially with 0:1:1, 2:48:50, 5:45:50, and 10:40:50 ethyl acetate:hexane:methylene chloride, to give further crude product as a tan solid (31.9 g). The combined crude product (82.5 g) was suspended in diethyl ether (400 mL), heated to reflux for 30 min, cooled and filtered to obtain methyl 4-(5-benzyloxycarbonylindol-3-ylmethyl)-3-methoxybenzoate as an ivory solid (46.1 g, 31%); partial NMR (250 MHz, $CDCl_3$): 3.84 (s, 3H, $CO_2CH_3$), 3.88 (s, $^3H$, $OCH_3$), 4.14 (s, 2H, $CH_2$), 5.35 (s, 2H, $OCH_2$), 6.97 (d, 1H, indole-H(2)), 8.15 (br, 1H, NH), 8.37 (s, 1H, indole-H(4)).

c. Methyl 4- (5-benzyloxycarbonyl-1-methylindol-3-ylmethyl)-3-methoxybenzoate.

A solution of methyl 4-(5-benzyloxycarbonylindol-3-ylmethyl)-3-methoxybenzoate (46 . 1 g) in N,N-dimethylformamide (200 mL) was added to a slurry of sodium hydride (2.83 g) in N,N-dimethylformamide (300 mL) at 5° C. under a nitrogen atmosphere. The mixture was stirred for 30 minutes at 5° C., then was treated with iodomethane (16.6 g), allowed to warm to room temperature and stirred for 16 hours. The reaction mixture was then poured into ice/water (400 mL), diluted with water (250 mL) and 1N hydrochloric acid (250 mL). The resulting aqueous solution was extracted with ethyl acetate. The combined organic extract was washed (1N hydrochloric acid, water, brine), dried ($MgSO_4$), filtered and evaporated. The residue was triturated with warm diethyl ether and filtered to give methyl 4-(5-benzyloxycarbonyl-1-methylindol-3-ylmethyl)-3-methoxybenzoate as an ivory solid (42.4 g, 89%); partial NMR (300 MHz, $CDCl_3$): 3.75 (s, 3H, $NCH_3$), 3.87 (s, 3H, $CO_2CH_3$), 3.90 (s, 3H, $OCH_3$), 4.12 (s, 2H, $CH_2$), 5.36 (s, 2H, $OCH_2$), 6.82 (s, 1H, indole-H(2)), 8.38 (d, 1H, indole-H(4)).

d. Methyl 4-(5-carboxy-1-methylindol-3-ylmethyl)-3-methoxybenzoate

A solution of methyl 4-(5-benzyloxycarbonyl-1-methylindol-3-ylmethyl)-3-methoxybenzoate (41.0 g) and formic acid (40 mL) in N,N-dimethylformamide (600 mL) was treated with 10% (w/w) palladium on carbon (10 g) and shaken under hydrogen (3.45 bar) for 24 hours. The catalyst was removed by filtration through diatomaceous earth and the filtrate evaporated to give an amber solid. The solid was triturated with warm diethyl ether and filtered to afford methyl 4-(5-carboxy-1-methylindol-3-ylmethyl)-3-methoxybenzoate as a light gray solid (28.9 g, 88%); mp 249°–251° C.; partial NMR (250 MHz, $DMSO-d_6$): 3.78 (s, 3H, $NCH_3$), 3.64 (s, 3H, $CO_2CH_3$), 3.93 (s, 3H, $OCH_3$), 4.09 (s, 2H, $CH_2$), 7.12 (s, 1H, indole-H(2)), 8.16 (s, 1H, indole-H(4)), 12.44 (br, 1H, $CO_2H$).

e. Methyl 3-methoxy-4-[1-methyl-5-(2-methyl-4,4,4-trifluorobutylcarbamoyl)indol-3-ylmethyl]benzoate A solution of methyl 4-(5-carboxy-1-methylindol-3-ylmethyl)-3-methoxybenzoate (2.0 g), 4-dimethylaminopyridine (0.71 g), 1-(3-dimethylaminopropyl)-3-ethylcarbodiimide hydrochloride (1.3 g), triethylamine (1.0 mL) and 4,4,4-trifluoro-2-methylbutylamine hydrochloride (1.2 g) in methylene chloride (28 mL) was stirred under a nitrogen atmosphere for 18 hours. The mixture was diluted with methylene chloride, washed (10% (w/v) hydrochloric acid, water and brine), dried ($MgSO_4$), and evaporated. The resulting ivory foam was purified by flash chromatography, eluting with 1:1 ethyl acetate:hexane to afford methyl 3-methoxy-4-[1-methyl-5-(2-methyl-4,4,4-trifluorobutylcarbamoyl)indol-3-ylmethyl]benzoate as a white powder (2.2 g, 82%); mp 168°–170° C.; partial NMR (300

MHz, CDCl₃): 1.12 (d, 3H, CHCH₃), 2.00 (m, 1H), 2.22 (m, 2H), 3.34–3.52 (m, 2H, NCH₂), 3.75 (s, 3H, NCH₃), 3.90 (s, 3H, CO₂CH₃), 3.93 (s, 3H, OCH₃), 4.13 (s, 2H, CH₂), 6.21 (t, 1H, NH), 6.82 (s, 1H, indole-H(2)), 8.02 (s, 1H, indole-H(4)).

f. 3-Methoxy-4-[1-methyl-5-(2-methyl-4,4,4-trifluorobutylcarbamoyl)indol-3-ylmethyl]benzoic acid A solution of methyl 3-methoxy-4-[1-methyl-5-(2-methyl-4,4,4-trifluorobutylcarbamoyl)indol-3-ylmethyl]benzoate (0.64 g) in methanol (3.5 mL), tetrahydrofuran (3.5 mL) and water (1.3 mL) was treated with lithium hydroxide monohydrate (0.34 g). The mixture was stirred for 18 hours and the organic solvents evaporated. The resulting aqueous solution was acidified with 10% (w/v) hydrochloric acid. The white precipitate which formed was collected by filtration, washed with water and dried under vacuum to give 3-methoxy-4-[1-methyl-5-(2-methyl-4,4,4-trifluorobutylcarbamoyl)indol-3-ylmethyl]benzoic acid as a white powder (0.55 g, 88%); partial NMR (300 MHz, DMSO-d₆): 1.00 (d, 3H, CHCH₃) 3.21 (m, 2H, NCH₂), 3.76 (s, 3H, NCH₃), 3.91 (s, 3H, OCH₃), 4.07 (s, 2H, CH₂), 7.15 (m, 2H, ArH), 7.46 (m, 3H, ArH), 7.68 (dd, 1H, ArH), 8.10 (d, 1H, ArH), 8.44 (t, 1H, NHCO).

The 4,4,4-trifluoro-2-methylbutylamine used in step e., above, was prepared as follows:

g. Ethyl 4,4,4-trifluoro-2-methylbutyrate

A solution of diisopropylamine (19.5 mL) in tetrahydrofuran (200 mL) at 0° C. was treated with n-butyllithium (71 mL, 1.5M in hexanes). The resulting solution was stirred for 30 minutes at 0° C., then was cooled to −70° C. A solution of ethyl 4,4,4-trifluorobutyrate (14 mL) in tetrahydrofuran (150 mL) was slowly added to the lithium diisopropylamide solution and the resulting mixture was stirred at −70° C. for 30 minutes. A solution of iodomethane (11.5 mL) in tetrahydrofuran was added in one portion, the cooling bath was removed, and the reaction mixture was allowed to warm to room temperature. The reaction mixture was quenched with water and evaporated. The residue was dissolved in methylene chloride, washed (10% (w/v) hydrochloric acid, water, and brine), dried (MgSO₄), filtered, and evaporated. The resulting pale yellow liquid was purified by distillation to yield ethyl 4,4,4-trifluoro-2-methylbutyrate as a colorless liquid (7.8 g, 46%); bp 125°–128° C.; partial NMR: (300 MHz, CDCl₃): 1.30 (m, 6H, CH₃), CH₂CH₃), 2.15 (m, 1H, H-C(3)), 2.64 (m, 1H, H-C(3)), 2.72 (m, 1H, H-C(2)), 4.16 (q, 2H, OCH₂).

h. 4,4,4-Trifluoro-2-methylbutyric acid

A solution of ethyl 4,4,4-trifluoro-2-methylbutyrate (7.7 g) in methanol (21 mL), tetrahydrofuran (21 mL) and water (8.4 mL) was treated with lithium hydroxide monohydrate (3.5 g). The mixture was stirred for 48 hours and the organic solvents evaporated. The resulting aqueous solution was diluted with water and acidified with 6N hydrochloric acid. The aqueous solution was exhaustively extracted with ethyl acetate. The combined organic extract was washed (water and brine), dried (MgSO₄), filtered and evaporated to give 4,4,4-trifluoro-2-methylbutyric acid as a pale yellow liquid (6.5 g, 99%); partial NMR (300 MHz, CDCl₃): 1.34 (d, 3H, CH₃), 2.18 (m, 1H, H-C(3)), 2.67, (m, 1H, H-C(3)), 2.74 (m, 1H, H-C(2)), 10.6 (br, 1H, CO₂H).

i. 4,4,4-Trifluoro-2-methylbutyramide

A solution of 4,4,4-trifluoro-2-methylburytic acid (6.5 g) in methylene chloride (42 mL) was added to a solution of 1,1-carbonyldiimidazole (7.5 g) in methylene chloride (40 mL). After gas evolution had subsided, the mixture was heated to reflux temperature for 30 minutes. The mixture was cooled to room temperature and anhydrous ammonia was bubbled through the mixture for 20 minutes. The reaction mixture was stirred for 18 hours at room temperature, then was diluted with ethyl acetate, washed (10% (v/v) hydrochloric acid, water and brine), dried (MgSO₄), filtered and evaporated. The solid residue was purified by recrystallization from diethyl ether:hexane to give 4,4,4-trifluoro-2-methylbutyramide as a white solid (4.4 g, 69%); mp 90.5°–91.5° C.; partial NMR (300 MHz, CDCl₃): 1.30 (d, 3H, CH₃), 2.13 (m, 1H, H-C(3)), 2.62 (m, 1H, H-C(3)), 2.71 (m, 1H, H-C(2)), 5.56 (br, 2H, CONH₂).

j. 4,4,4-Trifluoro-2-methylbutylamine hydrochloride

A solution of 4,4,4-trifluoro-2-methylbutyramide (3.3 g) in diethyl ether (50 mL) was added to a refluxing slurry of lithium aluminum hydride (1.2 g) in diethyl ether (50 mL) at such a rate to maintain reflux. The reaction was heated at reflux temperature for 2 hours, cooled to 0° C., and quenched by sequential addition of water (1.2 mL), 10% (w/v) aqueous sodium hydroxide solution (1.2 mL), and water (3.6 mL). The resulting suspension was filtered. The filtrate was dried (MgSO₄) and filtered. Anhydrous hydrogen chloride was bubbled through the filtrate for 5 minutes and the solvent evaporated to afford 4,4,4-trifluoro-2-methylbutylamine hydrochloride as a white solid (3.3 g, 88%); mp 224°–225° C.; partial NMR (300 MHz, DMSO-d₆): 1.04 (d, 3H, CH₃), 2.81–2.60 (br, 2H, NCH₂), 8.29 (br, 2H, NH₂).

An alternative preparation of the amine hydrochloride used in step e., above, is as follows:

k. 2-Methyl-4,4,4-trifluorobutyric acid

To sodium hexamethyldisilazane (0.945M in tetrahydrofuran) (667 mL, 0.63 mol) in tetrahydrofuran (0.9 L) at −78° C., under nitrogen, was added a solution of ethyl 4,4,4-trifluorobutyrate (90.6 mL) in tetrahydrofuran (100 mL). After stirring for 1.5 hour, to the vigorously stirred mixture was added methyl iodide (112 mL) as fast as possible. The reaction was warmed with a 0° C. bath for 2 hours. Methanol (1 L) and 1N lithium hydroxide (1.2 L) were added and stirring continued for 48 hours. The mixture was acidified with 2N hydrochloric acid and extracted with ethyl acetate. The combined organic phase was washed (brine), dried (MgSO₄), and evaporated at 30° C. After combination with product from separate conversions of ethyl 4,4,4-trifluorobutyrate (97.79 g), distillation afforded 2-methyl-4,4,4-trifluorobutyric acid (173.24 g, 96%) as a brown solid-liquid contaminated with 4,4,4-trifluorobutyric acid and 2,2-dimethyl-4,4,4-trifluorobutyric acid; bp 48.0°–108° C. (9,900 Pa); GLC: $t_R$=6.1 min.

l. 2-Methyl-4,4,4-trifluorobutyryl chloride

To 2-methyl-4,4,4-trifluorobutyric acid (172 g) in methylene chloride (150 mL) and N,N-dimethylformamide (3.5 mL) at 0° C., under nitrogen was added (dropwise) oxalyl chloride (125 mL). The mixture was allowed to warm to ambient temperature and stirred for 16 hours. After distillation of the solvent, distillation using a concentric tube distillation column (40 cm × 15 mm) afforded 2-methyl-4,4,4-trifluorobutyryl chloride (about 99% purity, 79.87 g, 42%); bp 115.0°–116.0° C. (at atmospheric pressure, measured at room temperature as 763.27 mm Hg); GLC: $t_R$=5.04 min; MS(CI): 139 (M+H-HCl).

m. 2-Methyl-4,4,4-trifluorobutyramide

Into 2-methyl-4,4,4-trifluorobutyryl chloride (35 g) in methylene chloride (300 mL) at 0° C., under nitrogen, was bubbled ammonia for 15 min. The mixture was stirred for 1 hour at 0° C. and then at ambient temperature for for 16 hours before ethyl acetate (600 mL) and 1:1 v/v 10% hydrochloric acid:brine (500 mL) were added. After separating the organic layer, the aqueous layer was basified with 1N sodium hydroxide and extracted with ethyl acetate. The organic extract was dried (MgSO$_4$) and evaporated. The residue was combined with the product of an identical reaction. The combined solid was dissolved in ethyl acetate (200 mL) and added to hexane (2 L) to afford 2-methyl-4,4,4-trifluorobutyramide (56.9 g, 91%) as a colorless solid; mp 90.5°–91.5° C.; GLC: $t_R$=12.04 min, MS(CI): 156 (M+H).

Analysis for $C_5H_8F_3NO$: Calculated: C, 38.72; H, 5.20; N, 9.03 Found: C, 38.59; H, 5.11; N, 8.56 n. 2-Methyl-4,4,4-trifluorobutylamine hydrochloride

To a suspension of lithium aluminum hydride (15.5 g) in diethyl ether (290 ml) was added a solution of 2-methyl-4,4,4-trifluorobutyramide (31.74 g) in diethyl ether (0.5 L) at a rate to obtain a gentle reflux. After heating at reflux for 12 hours and cooling to 0° C., the reaction was quenched with saturated sodium sulfate solution and allowed to warm to ambient temperature. The mixture was dried (Na$_2$SO$_4$) and filtered through diatomaceous earth with diethyl ether wash. The filtrate was treated with gaseous hydrochloric acid (14.9 g, 0.409 mol) and then the solvent was evaporated. The residue was dissolved in methylene chloride and combined with product from a similar reaction of 2-methyl-4,4,4-trifluorobutyramide (25 g). Recrystallization from methylene chloride and diethyl ether, followed by trituration with ethyl acetate, afforded 2-methyl-4,4,4-trifluorobutylamine hydrochloride (51.35 g, 79%) as a light pink solid; mp 224.5°–225.5° C.; MS(CI): 142 (M+H-HCl).

Analysis for $C_5H_{11}ClF_3N$: Calculated: C, 33.81; H, 6.24; N, 7.89 Found: C, 33.93; H, 6.13; N, 8.17

EXAMPLE 2

(R)-3-Methoxy-4-[1-methyl-5-(2-methyl-4,4,4-trifluorobutylcarbamoyl)indol-3-ylmethyl]-N-(2-methylphenylsulfonyl)benzamide A mixture of (R)-3-methoxy-4-[1-methyl-5-(2-methyl-4,4,4-trifluorobutylcarbamoyl)indol-3-ylmethyl]benzoic acid (14.28 g), 4-dimethylaminopyridine (4.39 g), 1-(3-dimethylaminopropyl)-3-ethylcarbodiimide hydrochloride (8.34 g) and 2-methylbenzenesulfonamide (5.85 g) was dissolved in dry methylene chloride (270 mL) and the solution was stirred under an inert atmosphere for 48 h. The mixture was diluted with methylene chloride (300 mL) and washed three times with 1N hydrochloric acid. The combined hydrochloric washes were back washed with methylene chloride. The combined organic extracts were washed twice with water and evaporated. The residue was dissolved in a small volume of methanol and 1N sodium hydroxide and this solution was purified by flash chromatography over octadecylsilyl bonded silica gel ("Regis PREP-40-ODS" -irregularly shaped 32–74μ diameter particles, 72% silanol coverage, 21% carbon load) (450 g) eluting with 50:50 methanol:water, pH 7.1. The appropriate fractions (TLC, $R_f$=0.73, octadecylsilyl bonded silica gel, 200μ layer, 12% carbon load, 80:20 methanol:water, pH 6.1, 0.1% ammonium acetate buffer) were combined, the methanol evaporated, and the residual aqueous solution acidified to pH 1 with 1N hydrochloric acid. The resultant precipitate was filtered, washed (water), and dried under vacuum to give the title compound (16.7 g, 88%) as a white solid; mp 117°–120° C.; ee at least 99%.

Analysis for $C_{31}H_{32}F_3N_3O_5S$: Calculated: C, 60.48; H, 5.24; N, 6.83 Found: C, 60.32; H, 5.32; N, 6.66

The starting benzoic acid was prepared as follows:
a. 4,4,4-Trifluorobutyric acid A solution of lithium hydroxide monohydrate (324 g) in water (1.8 L) was added to a stirred solution of ethyl 4,4,4-trifluorobutyrate (436 g) in methanol (2.0 L) and dry tetrahydrofuran (2.0 L) and the suspension was stirred overnight. After the suspension was partially evaporated, the residue was diluted with water and washed with diethyl ether. The aqueous layer was acidified with 6M hydrochloric acid and extracted with diethyl ether. The combined extracts were washed (brine), dried (MgSO4), and filtered. The filtrate was evaporated and the residue distilled (bp 165°–168° C.) to give 4,4,4-trifluorobutyric acid (347 g, 95%); mp 27°–30° C.; partial NMR; (300 MHz, CDCl$_3$): 2.33–2.57 (m, 2H, CF$_3$CH$_2$), 2.66 (t, 2H, CH$_2$CO$_2$H).

b. 4,4,4-Trifluorobutyryl chloride

Dimethyl formamide (1.0 mL) and oxalylchloride (239 mL) were added to a 0° C. solution of 4,4,4-trifluorobutyric acid (343 g) in dry methylene chloride (230 mL) and warmed to room temperature overnight. The methylene chloride was removed by distillation and the residue distilled to yield 4,4,4-trifluorobutyryl chloride (328 g, 85%); bp 103°–106° C.; partial NMR (300 MHz, CDCl$_3$): 2.47–2.64 (m, 2H, CF$_3$CH$_2$) 3.19 (t, H, CH$_2$COCl).

c. (4R,5S)-4-Methyl-3-(4,4,4-trifluorobutyryl)-5-phenyl-2-oxazolidinone

A solution of n-butyllithium (2.0 mole) in hexane was added to a stirred solution of (4R,5S)-(+)-4-methyl-5-phenyl-2-oxazolidinone (353 g) in dry tetrahydrofuran (2500 mL) at −78° C. under an inert atmosphere. The solution was stirred at −70° C. for 15 min, then 4,4,4-trifluorobutyryl chloride (320 g) was added over 30 min at −60° C. and the mixture warmed to room temperature and stirred overnight. The mixture was evaporated and the residue was partitioned between diethyl ether and water. The ethereal layer was washed (1N hydrochloric acid, brine (twice)), dried (MgSO$_4$), and evaporated to yield crude product (604 g, about 100%). Filtration through 3000 mL of silica gel using 1:1 methylene chloride:hexanes as the eluent afforded a white solid. Recrystallization from methylene chloride:hexanes afforded (4R,5S)-4-methyl-3-(4,4,4-trifluorobutyryl)-5-phenyl-2-oxazolidinone (519 g, 86%); mp 93°–95° C.; partial NMR (300 MHz, CDCl$_3$): 0.91 (d, 3H, CH$_3$), 2.45–2.65 (m, 2H, CF$_3$CH$_2$), 3.18–3.40 (m, 2H, CH$_2$CO), 4.78 (m, 1H, 4-H oxazolidinone), 5.70 (d, 1H, 5-H oxazolidone), 7.30–7.44 (m, 5H, Ar).

d. (4R,5S)-4-Methyl-3-((2R)-2-methyl-4,4,4-trifluorobutyryl)-5-phenyl-2-oxazolidinone To a stirred solution of sodium bis(trimethylsilyl)amide (1.9 mole) in tetrahydrofuran (1900 mL) cooled to −40° C. was added a solution of (4R,5S)-4-methyl-3-(4,4,4-trifluorobutyryl)-5-phenyl-2-oxazolidinone (517 g) in dry tetrahydrofuran (800 mL) under an inert atmosphere. The mixture was maintained at −40° C. for one-half hour, and warmed to −35° C. over an additional one-half hour. To this mixture was added iodomethane (142 mL) over approximately 15 min while maintaining the internal reaction temperature between −35° C. and −30° C. The mixture was stirred for an additional 2 h at −30° C. and the cold reaction mixture was poured over chilled aqueous ammonium chloride (700 g in 2 L water). The mixture was diluted with diethyl ether (1 L) and the layers separated. The organic layer was washed (25% w/v aqueous sodium bisulfate, brine). The aqueous portions were extracted with 1:1 methylene chloride:diethyl ether and methylene chloride. The combined organic layers were dried (MgSO$_4$) and evaporated to afford crude product (595 g) as a reddish oil. Filtration through silica gel (3000 mL), using a gradient of 1–5% ethyl acetate in hexanes, followed by evaporation, afforded a white solid (490 g) which was a mixture of the named product, the diastereomeric methylated side product and unmethylated starting material. Crystallization from diethyl ether:hexanes afforded (4R,5S)-4-methyl-3-((2R)-2-methyl-4,4,4-trifluorobutyryl)-5-phenyl-2-oxazolidinone (370 g, 68%) as a white solid; mp 68°–70° C. Analysis by HPLC (Zorbax silica gel, 4.6 mm×25 cm, 1:9 ethyl acetate:-hexanes, FR=1.5 ml/min, UV detector at 254 nm) showed this sample to be about 99% pure (retention volume=2.6). A second recrystallization of this white solid from diethyl ether:hexanes afforded an analytical sample of (4R,5S)-4-methyl-3-((2R)-2-methyl-4,4,4-trifluorobutyryl)-5-phenyl-2-oxazolidinone (300 g, 55%) as transparent colorless needles; mp 74.5°–75° C.; partial NMR (300 MHz, CDCl$_3$): 0.89 (d, 3H, 4-CH$_3$ of oxazolidinone), 1.33 (d, 3H, CH(CH$_3$)CO), 2.10–2.31 (m, 1H, CF$_3$CH$_2$), 2.74–2.97 (m, 1H, CF$_3$CH$_2$), 4.03–4.17 (m, 1H, CHCO), 4.79 (m, 1H, 4-H of oxazolidinone), 5.71 (d, 1H, 5-H of oxazolidinone), 7.26–7.44 (m, 5H, phenyl). HPLC analysis as above showed 99.9% purity.

Analysis for C$_{15}$H$_{16}$F$_3$NO$_3$: Calculated: C, 57.14; H, 5.11; N, 4.44 Found: C, 57.17; H, 5.16; N, 4.59 e. (R)-2-Methyl-4,4,4-trifluorobutan-1-ol

Lithium aluminum hydride (10.26 g) was added to a stirred solution of (4R,5S)-4-methyl-3-((2R)-2-methyl-4,4,4-trifluorobutyryl)-5-phenyl-2-oxazolidinone (28 g) in dry diethyl ether (200 mL) at −20° C. under an inert atmosphere, then the mixture was warmed to 0° C. After 2 h at 0° C., water (10.27 mL), 10% w/v sodium hydroxide(10.27 mL) and water (31 mL) were added, and the mixture was stirred 20 min. The salts were filtered and washed with distilled diethyl ether. The diethyl ether solution was dried (K$_2$CO$_3$) and diluted with pentane. This resulted in precipitation of recovered (4R,5S)-(+)-4-methyl-5-phenyl-2-oxazolidinone which was isolated by filtration. Concentration of the filtrate by distillation afforded several fractions. The first fractions (bath temperature to 60° C.) were pentane and diethyl ether; a second set of fractions (bath temperature 60° C. to 100° C.) was 12 g of a oil that was a 40:60 mixture of (R)-2-methyl-4,4,4-trifluorobutan-1-ol (calculated as 4.8 g alcohol) and diethyl ether by NMR. Warming the remaining tarry residue (bath temperature 85° C.) under vacuum (13,330 Pa) afforded an additional 7.2 g of (R)-2-methyl-4,4,4-trifluorobutan-1-ol (total yield, 12.0 g, 94%); partial NMR (300 MHz, CDCl$_3$-D$_2$O shake): 1.06 (d, 3H, CH$_3$), 1.41 (br t, 1H, OH), 1.86–2.07 (m, 2H, CH(CH$_3$) plus one CF$_3$CH$_2$), 2.31–2.42 (m, 1H, one CF$_3$CH$_2$), 3.49 (dd, 1H, one CH$_2$OH), 3.58 (dd, 1H, one CH$_2$OH).

f. (R)-2-(2-Methyl-4,4,4-trifluorobutyl)-1H-isoindol-1,3(2H)-dione

Diethyl azodicarboxylate (15.4 mL) was added to a 0° C., stirred slurry of (R)-2-methyl-4,4,4-trifluorobutan-1-ol (about 12.0 g), phthalimide (13.4 g), and triphenylphosphine (23.7 g) in diethyl ether (about 6.5 g, see above) and dry tetrahydrofuran (110 mL), warmed to rook temperature overnight, and stirred an additional 8 h. The mixture was evaporated, methylene chloride was added to the residue, and the slurry was filtered. The filtrate was purified by flash chromatography, eluting with 1:1 methylene chloride:hexanes, to give (R)-2-(2-methyl-4,4,4-trifluorobutyl)-1H-isoindol-1,3(2H)-dione (17.1 g, 75%) as a white solid; mp 45°–47 ° C.; partial NMR (400 MHz, CDCl$_3$): 1.08 (d, 3H, CH$_3$), 1.94–2.07 (m, 1H, CF$_3$CH$_2$), 2.14–2.31 (m, 1H, CF$_3$CH$_2$), 2.36–2.50 (m, 1H, CHCH$_3$), 3.58 (dd, 1H, CH$_2$N), 3.64 (dd, 1H, CH$_2$N).

g. (R)-2-Methyl-4,4,4-trifluorobutylamine hydrochloride

Hydrazine monohydrate (3.1 mL) was added to a stirred solution of (R)-2-(2-methyl-4,4,4-trifluorobutyl)-1H-isoindole-1,3(2H)-dione (17.1 g) in anhydrous ethanol (85 mL) and heated to reflux. After three hours' reflux, the solution was cooled; ethanol (40 mL) was added; and the solution was acidified to pH 1 by addition of concentrated hydrochloric acid and was filtered. The filtrate was evaporated, and the residue was purified by sublimation (bath temperature 170° C., at 6.6 Pa) to yield (R)-2-methyl-4,4,4-trifluorobutylamine hydrochloride as a white solid (9.89 g, 88%); mp 187°–191° C.; partial NMR (300 MHz, DMSO-d$_6$, D$_2$O shake): 1.05 (d, 3H, CH$_3$), 2.06–2.36 (m, 2H, CF$_3$CH$_2$) 2.36–2.54 (m, 1H, CHCH$_3$) 2.73 (dd, 1H, CH$_2$N), 2.87 (dd, 1H, CH$_2$N) 8.20 (br s, 2H, NH$_2$).

h. Methyl (R)-3-methoxy-4-[1-methyl-5-(2-methyl-4,4,4-trifluorobutylcarbamoyl)indol-3-ylmethyl]benzoate A mixture of (R)-2-methyl-4,4,4-trifluorobutylamine hydrochloride (9.79 g), methyl 4-(5-carboxy-1-methylindol-3-ylmethyl)-3-methoxybenzoate (20.55 g), 4-dimethylaminopyridine (7.45 g), 1-(3-dimethylaminopropyl)-3-ethylcarbodiimide hydrochloride (15.07 g) and triethylamine (9.3 mL) was dissolved in dry methylene chloride (240 mL) and the solution was stirred under an inert atmosphere for 18 h. The mixture was diluted with methylene chloride (200 mL) and washed twice with 1N hydrochloric acid. The combined acid washes were back extracted with methylene chloride and the combined organic extracts were washed (water, brine), dried (MgSO$_4$), and evaporated. The residue was purified by flash chromatography, eluting with 97:3 methylene chloride:ethyl acetate to give methyl (R)-3-methoxy-4-[1-methyl-5-(2-methyl-4,4,4-trifluorobutylcarbamoyl)indol-3-ylmethyl]benzoate (14.48 g, 55%) as a white solid; mp 150°–151° C.; partial NMR (300 MHz, CDCl$_3$): 1.12 (d, 3H, CH$_3$), 1.98–2.08 (m, 1H, CHCH$_3$) 2.12–2.44 (m, 2H, CF$_3$CH$_2$), 3.30–3.58 (m, 2H, CH$_2$N), 3.76 (s, 3H, NCH$_3$), 3.90 (s, 3H, OCH$_3$), 3.93 (s, 3H, OCH$_3$), 4.13 (s, 2H, ArCH$_2$Ar'), 6.23 (br t, 1H, NHCO).

i. (R)-3-Methoxy-4-[1-methyl-5-(2-methyl-4,4,4-trifluorobutylcarbamoyl)indol-3-ylmethyl]benzoic acid A solution of lithium hydroxide monohydrate (7.68 g) in water (50 mL) was added to a stirred solution of methyl (R)-3-methoxy-4-[1-methyl-5-(2-methyl-4,4,4-trifluorobutylcarbamoyl)indol-3-ylmethyl]benzoate (14.38 g) in methanol (120 mL) and distilled tetrahydrofuran (120 mL) under an inert atmosphere. After 18 h the solvent was evaporated, the residue was dissolved in water (250 mL) and distilled tetrahydrofuran (23 mL), acidified to pH 1 by addition of concentrated hydrochloric acid, and diluted with water (150 mL). The precipitate was collected and washed with water to give (R)-3-methoxy-4-[1-methyl-5-(2-methyl-4,4,4-trifluorobutylcarbamoyl)indol-3-ylmethyl]benzoic acid (14.28 g, 100%); mp 218°–223° C.; partial NMR (300 MHz, DMSO-$d_6$): 1.00 (d, 3H, $CH_3$), 2.04–2.28 (m, 2H, $CF_3CH_2$), 2.32–2.44 (m, 1H, $CHCH_3$), 3.21 (br t, 2H, $CH_2N$), 3.76 (s, 3H, $NCH_3$), 3.90 (s, 3H, $OCH_3$), 4.07 (s, 2H, $ArCH_2Ar'$), 8.43 (br t, 1H, NHCO).

EXAMPLE 3

(R)-3-Methoxy-4-[1-methyl-5-(2-methyl-4,4,4-trifluorobutylcarbamoyl)indol-3-ylmethyl]-N-(2-methylphenylsulfonyl)benzamide To a mixture of 4-(5-carboxy-1-methylindol-3-ylmethyl)-3-methoxy-N-(2-methylphenylsulfonyl)benzamide (103.5 g), 4-dimethylaminopyridine (112.4 g), and 1-(3-dimethylaminopropyl)-3-ethylcarbodiimide hydrochloride (51.8 g) in tetrahydrofuran (distilled from sodium benzophenone ketyl) (2.0 L), which had been stirred for 2 hours, was added (R)-2-methyl-4,4,4-trifluorobutylamine hydrochloride (42.6 g); and the reaction mixture was stirred overnight (about 18 hours, incomplete reaction) then heated to reflux for two hours (complete reaction). The cooled reaction mixture was diluted with ethyl acetate (2 L) washed with 1N hydrochloric acid (twice) and brine, dried ($MgSO_4$) and evaporated. The residue (138.6 g) was combined with impure product from similar procedures (28.0 g) and purified by flash chromatography, eluting with methylene chloride:ethyl acetate (sequentially, 1:0, 9:1 and 3:1) to afford a solid which was triturated twice with ether to give the crude title compound (135.2 g) which was recrystallized from ethanol (1.2 L) and acetone (0.3 L) (concentrated by boiling to about 0.9 L and refrigerated) and dried under vacuum to provide the title compound (117.1 g, 65% recovery) as a white crystalline solid; mp 141.5°–143.5° C.; NMR (300 MHz, DMSO-$d_6$): 1.01 (d, 3H, $CH_3$), 2.0–2.2 (m, 2H, $CF_3CH_2$), 2.3–2.5 (m, 1H, $CHCH_3$), 2.61 (s, 3H, $ArCH_3$), 3.23 (br t, 2H, $CH_2N$), 3.76 (s, 3H, $NCH_3$), 3.92 (s, 3H, $OCH_3$), 4.07 (s, $ArCH_2Ar'$), 7.13 (s, 1H), 7.17 (d, 2H), 7.38–7.69 (m, 6H), 7.72 (d, 1H), 8.05 (d, 1H), 8.11 (s, 1H), 8.46 (br t, 1H, NHCO).

Analysis for $C_{31}H_{32}F_3N_3O_5S$: Calculated: C, 60.48; H, 5.24; N, 6.83 Found: C, 60.47; H, 5.27; N, 6.67

The starting material 5-carboxyindole derivative may be prepared as follows:

a. 4-(5-Methoxycarbonyl-1-methylindol-3-ylmethyl)-3-methoxybenzoic acid

To a solution of methyl 4-(5-methoxycarbonyl-1-methylindol-3-ylmethyl)-3-methoxybenzoate (105.1 g) in tetrahydrofuran (1.4 L) was added methanol (450 mL) and deionized water (450 mL), followed by an equimolar amount of lithium hydroxide monohydrate (12.00 g). After the reaction mixture had stirred about 20 hours, it was acidified to pH 2 by addition of 6N hydrochloric acid (60 ml). Evaporation of the organic solvents resulted in the precipitation of a crude product (104.2 g) which was filtered and dried under vacuum before it was recrystallized by dissolving it in boiling tetrahydrofuran (600 mL), addition of toluene (about 1.2 L) and concentration to about one liter. Following cooling and stirring overnight, filtration, and drying under vacuum, a first crop is (71.1 g) was obtained. A second, similar recrystallization of this material from tetrahydrofuran (500 mL) and toluene (1 L) afforded 4-(5-methoxycarbonyl-1-methylindol-3-ylmethyl)-3-methoxybenzoic acid (58.3 g, 57.7%) as an off-white solid; NMR (300 MHz, DMSO-$d_6$): 3.78 (s, 3H, $NCH_3$), 3.83 (s, 3H, $CO_2CH_3$), 3.92 (s, 3H, $OCH_3$), 4.07 (s, $ArCH_2Ar'$), 7.17 (d, 1H), 7.18 (s, 1H), 7.43–7.50 (m, 3H), 7.75 (dd, 1H), 8.19 (d, 1H); the same benzoic acid obtained by a similar procedure, but purified by flash chromatography, eluting with (methylene chloride:tetrahydrofuran:acetic acid (sequentially, 1:0:0, 1:9:0, and 0:400:1) followed by isolation and drying under vacuum of crystals formed on standing in methylene chloride:tetrahydrofuran fractions, had mp 228.0°–229.5° C. An additional amount of the benzoic acid (23.6 g, 23.3%), as well as recovered diester (11.5 g, 10.7%), was obtained by concentration and flash chromatography of the mother liquors, eluting with methylene chloride:tetrahydrofuran (sequentially, 1:0, 3:1, 2:1).

b. 4-(5-Methoxycarbonyl-1-methylindol-3-ylmethyl)-3-methoxy-N-(2-methylphenylsulfonyl)benzamide To a solution of 4-(5-methoxycarbonyl-1-methylindol-3-ylmethyl)-3-methoxybenzoic acid (125.9 g) in tetrahydrofuran (3.0 L, distilled from sodium benzophenone ketyl) (prepared by heating at 50° C. until dissolution was complete, followed by cooling to room temperature with an ice-water bath) was added 4-dimethylaminopyridine (56.6 g) and 1-(3-dimethylaminopropyl)-3-ethylcarbodiimide hydrochloride (102.4 g), and the mixture was stirred one hour. To the mixture was added 2-methylbenzenesulfonamide (67.1 g), and the reaction mixture was stirred about 3 days (for convenience). The reaction mixture was diluted with ethyl acetate (2.0 L) and washed with 1N hydrochloric acid (twice) and brine (3 times, until neutral), and the aqueous extracts were back washed with ethyl acetate. The combined ethyl acetate solution was dried ($MgSO_4$), and partially evaporated to give a slurry of solid in ethyl acetate (about 0.5 L) which was refrigerated overnight. Collection of the solid afforded the crude product (158.5 g, 88%, essentially pure by TLC) as a light pink solid. Recrystallization by dissolution in hot tetrahydrofuran (1.5 L), filtration while hot, dilution with ethyl acetate (2.0 L), and boiling down to a final volume of about 2.5 L afforded a first crop of 4-(5-methoxycarbonyl-1-methylindol-3-ylmethyl)-3-methoxy-N-(2-methylphenylsulfonyl)benzamide (105.5 g, 59%) as a white solid; mp 211°–213° C.; NMR (250 MHz, DMSO-$d_6$): 2.60 (s, 3H, $ArCH_3$), 3.76 (s, 3H, $NCH_3$), 3.82 (s, 3H, $CO_2CH_3$), 3.92 (s, 3H, $ArOCH_3$), 4.04 (s, 2H, $ArCH_2Ar'$), 7.15 (d, 1H), 7.22 (s, 1H), 7.38–7.58 (m, 6H), 7.75 (dd, 1H), 8.03 (dd, 1H), 8.17 (d, 1H). (Two additional crops (35.5 g, 20%) and crude product (39.5 g) from concentration of the mother liquors were also obtained.)

c. 4-(5-Carboxy-1-methylindol-3-ylmethyl)-3-methoxy-N-(2-methylphenylsulfonyl)benzamide A mixture of 4-(5-methoxycarbonyl-1-methylindol-3-ylmethyl)-3-methoxy-N-(2-methylphenylsulfonyl)benzamide (130.0 g), tetrahydrofuran (1.0 L) and 1N sodium hydroxide (1.0 L) was heated to about 60° C. overnight, then treated with additional 1N sodium hydroxide (200 mL) and heated an additional 5 hours at 60° C. (likely unnecessary). The cooled reaction mixture was acidified with 6N hydrochloric acid (250 mL) and extracted with ethyl acetate. The ethyl acetate solution was washed with brine (three times), dried ($MgSO_4$) and evaporated to give a solid which was dried at 50° C. under vacuum to give 4-(5-carboxy-1-methylindol-3-ylmethyl)-3-methoxy-N-(2-methylphenylsulfonyl)benzamide (12.9 g, 100% when calculated as 0.45 hydrate), mp 255°–257° C.; NMR (300

MHz, DMSO-d$_6$): 2.60 (s, 3H, ArCH$_3$), 3.76 (s, 3H, NCH$_3$), 3.91 (s, 3H, OCH$_3$), 4.05 (s, 2H, ArCH$_2$Ar'), 7.15 (d, 1H), 7.19 (s, 1H), 7.39–7.51 (m, 5H), 7.58 (br t, 1H), 7.72 (dd, 1H), 8.03 (dd, 1H), 8.14 (d, 1H).

Anaylsis for C$_{26}$H$_{24}$N$_2$O$_6$S.0.45 H$_2$O: Calculated: C, 62.37; H, 5.01; N, 5.60 Found: C, 62.60; H, 5.03; N, 5.52

Methyl 4-(5-methoxycarbonyl-1-methylindol-3-ylmethyl)-3-methoxybenzoate, used in step a., above, may be obtained from methyl indole-5-carboxylate and methyl 4-bromomethyl-3-methoxybenzoate using a similar procedure to that described above in Example 1.b, followed by methylation using a similar procedure to that described above in Example 1.c. Methyl 4-(5-methoxycarbonyl-1-methylindol-3-ylmethyl)-3-methoxybenzoate, obtained by esterification of 4-(5-carboxy-1-methylindol-3-ylmethyl)-3-methoxybenzoic acid with methanol and acetyl chloride, followed by filtration through a bed of silica gel, eluting with methylene chloride in a continuous extractor, evaporation and trituration with ether, had mp 138°–139° C.

An alternative preparation of 4-(5-carboxy-1-methylindol-3-ylmethyl)-3-methoxy-N-(2-methylphenylsulfonyl)benzamide is as follows:

d. Methyl 3-methyl-4-nitrobenzoate

To a stirred suspension of 3-methyl-4-nitrobenzoic acid (100 g, 0.55 mole) in methanol (400 mL) was added thionyl chloride (36 g, 0.30 mole), over a period of 1 hour (the temperature of the reaction mixture rising to about 35°–40° C.). The mixture was heated to reflux for 1.5 hours, then cooled to 50°–55° C. and maintained at this temperature for 30 minutes prior to cooling to ambient temperature. Water (100 mL) was added over 30 minutes, with cooling applied to maintain the temperature at 20°–25° C. Filtration was followed by washing of the solid with water (100 mL twice), and drying at 40° C. under vacuum, to afford 103 g (95%) of methyl 3-methyl-4-nitrobenzoate as a yellow solid; mp 83°–85° C.; NMR (250 MHz, CDCl$_3$): 2.62 (s, 3H, ARCH$_3$), 3.98 (s, 3H, CO$_2$CH$_3$), 8.01 (m, 3H).

e. 5-Methoxycarbonyl-2-nitro-β-(1-pyrrolidinyl)-styrene and 5-methoxycarbonyl-2-nitro-β-(dimethylamino)styrene A mixture of a product prepared according to Example 3.d., above, (1000 g, 5.13 mole), N,N-dimethylformamide dimethyl acetal (1219 g, 10.26 mole) and pyrrolidine (382 g, 5.38 mole) in N,N-dimethylformamide (3000 mL) was heated to reflux over about 45 minutes and maintained at a gentle reflux for 2.5 hours. After the reaction mixture was cooled to ambient temperature, it was added over 20 minutes to 10 L of ice/water. The resulting slurry was stirred for 30 minutes prior to filtration and washing of the solid with cold water (1500 mL three times). Drying at 50° C. under vacuum afforded 1208 g (83.3%) of an 82:18 mixture of 5-methoxycarbonyl-2-nitro-β-(1-pyrrolidinyl)styrene and 5-methoxycarbonyl-2-nitro-β-(dimethylamino)styrene as a dark red solid; mp 109°–112° C.; NMR (250 MHz, CDCl$_3$): 1.97 (m, 0.82 of 4H), 2.95 (s, 0.18 of 6H, N(CH$_3$)$_2$), 3.37 (m, 0.82 of 4H), 3.93 (s, 3H, CO$_2$CH$_3$), 5.77 (d, 0.82 of 1H), 5.78 (d, 0.18 of 1H), 7.08 (d, 0.18 of 1H), 7.39 (d, 0.82 of 1H), 7.49 (dd, 0.82 of 1H), 7.53 (dd, 0.18 of 1H), 7.82 (d, 1H), 8.13 (m, 1H).

f. 2-(5-Methoxycarbonyl-2-nitrophenyl)-2-(2-methoxy-4-methoxycarbonylbenzyl)acetaldehyde The product of Example 3.e., above, (800 g, 2.95 mole) and methyl 4-bromomethyl-3-methoxybenzoate (770 g, 2.97 mole) in acetonitrile (2000 mL) were heated to reflux over 20 minutes and held at this temperature for 50 minutes. More benzoate (35 g, 0.135 mole) was then added and heating continued for a total of 4 hours. After cooling to ambient temperature, the mixture was diluted with water (2000 mL), added over 5 minutes, during which time a dark brown solid precipitated. The mixture was stirred for 30 minutes and filtered, the precipitate being washed with acetonitrile (500 mL) and dried at 45° C. under vacuum. This afforded 2-(5-methoxycarbonyl-2-nitrophenyl)-2-(2-methoxy-4-methoxycarbonylbenzyl)acetaldehyde (914.5 g, 77.3%) as a pale brown solid; mp 117°–120° C.; NMR (250 MHz, CDCl$_3$): 3.11 (dd, 1H), 3.50 (dd, 1H), 3.82, 3.90, 3.97 (each s, 3H, OCH$_3$ plus 2 CO$_2$CH$_3$ groups), 4.65 (dd, 1H), 7.00 (d, 1H), 7.46 (m, 2H), 7.88 (d, 1H), 7.93 (d, 1H), 8.04 (dd, 1H), 9.82 (s, 1H).

g. Methyl 4-(5-methoxycarbonylindol-3-ylmethyl)-3-methoxybenzoate

A stirred suspension of the product of Example 3.f., above, (600 g, 1.49 mole) and iron powder (600 g, 10.7 mole) in acetic acid (2.2 L) and toluene (3.8 L) was heated carefully to reflux. An exotherm occurred at 95° C., resulting in the mixture reaching reflux without external heating. Heating was then applied as necessary to maintain reflux for a total of 2 hours. The mixture was allowed to cool to ambient temperature, and then cooled at 5° C. for 30 minutes prior to filtration and washing of the solid with toluene (200 mL twice). The combined filtrates and washings were washed with 15% brine (3.8 L) and 5% sodium bicarbonate solution (3.8 L), and evaporated. The resulting solid was recrystallised from methanol (2 L) to afford methyl 4-(5-methoxycarbonylindol-3-ylmethyl)-3-methoxybenzoate (420 g, 79.9%); mp 136°–138° C.; NMR (250 MHz, CDCl$_3$): 3.88, 3.90, 3.92 (each s, 3H, OCH$_3$ plus 2 CO$_2$CH$_3$ groups), 4.16 (s, 2H, ArCH$_2$Ar'), 6.98 (d, 1H), 7.12 (d, 1H), 7.33 (d, 1H), 7.52 (m, 2H), 7.89 (dd, 1H), 8.30 (br s, 1H), 8.36 (d, 1H).

h. Methyl 4-(5-methoxycarbonyl-1-methylindol-3-ylmethyl)-3-methoxybenzoate

To a stirred solution of the product of Example 3.g., above, (50 g, 142 mmole) and methyl iodide (87.5 mL, 1.42 mole) in tetrahydrofuran (333 mL) was added concentrated sodium hydroxide liquor (40 mL, 0.71 mole). After 7.5 hours water (200 mL) was added, and the organic layer separated and washed with brine (150 mL) and finally water (150 mL). After removal of 300 mL distillate under reduced pressure, a solid which precipitated was collected by filtration and washed with hexane (50 mL). Drying of the beige solid at 40° C. under vacuum afforded 48.0 g (91.3%) of methyl 4-(5-methoxycarbonyl-1-methylindol-3-ylmethyl)-3-methoxybenzoate; mp 137°–140° C.; NMR (250 MHz, DMSO-d$_6$): 3.91 (s, 3H, N-CH$_3$), 3.98 (s, 6H, 2 CO$_2$CH$_3$ groups), 4.07 (s, 3H, OCH$_3$), 4.22 (s, 2H, ArCH$_2$Ar'), 7.34 (m, 2H), 7.61 (m, 3H), 7.90 (dd, 1H), 8.33 (d, 1H).

i. 4-(5-Methoxycarbonyl-1-methylindol-3-ylmethyl)-3-methoxybenzoic acid

To a solution of the product of Example 3.h., above, (33.50 g, 91.3 mmole) in tetrahydrofuran (335 mL) and methanol (100 mL) was added water (67 mL) and lithium hydroxide monohydrate (4.025 g, 95.8 mmole). After the reaction mixture had stirred at ambient temperature for about 20 hours, it was heated to reflux and about 250 mL distillate collected. The residual solution was cooled to room temperature, diluted with water (210 mL) and toluene (210 mL), and the organic layer separated and extracted with water (40 mL). Combined aqueous layers were treated dropwise with acetic acid (4.18 mL, 73.0 mmole) and stirred for about 30 minutes prior to collection of the precipitate by filtration. After washing with water (67 mL twice) and methanol (67 mL twice), 4-(5-methoxycarbonyl-1-methylindol-3-ylmethyl)-3-methoxybenzoic acid (28.07 g, 84.1%) was obtained as a white solid; mp 228°–230° C.; NMR (250 MHz, DMSO-$d_6$): 3.77, 3.83, 3.93 (each s, 3H, OCH$_3$ plus NCH$_3$ plus CO$_2$CH$_3$), 4.08 (s, 2H, ArCH$_2$Ar'), 7.17 (d, 1H), 7.23 (s, 1H), 7.49 (m, 3H), 7.77 (dd, 1H), 8.21 (d, 1H).

j. 4-(5-Methoxycarbonyl-1-methylindol-3-ylmethyl)-3-methoxybenzoyl chloride

A solution of thionyl chloride (2.42 mL, 33 mmole) in dichloromethane (10 mL) was added dropwise over 5 minutes to a suspension of the product of Example 3.i, above, (10.59 g, 30 mmole) in dichloromethane (90 mL) containing N,N-dimethylformamide (0.2 mL), stirred at reflux under an atmosphere of nitrogen. After 2 hours, solvent was removed from the resulting yellow solution by distillation, approximately 85 mL of distillate being collected. Dilution of the residue with methyl t-butyl ether was followed by stirring at 15° C. for 30 minutes prior to collection of the solid precipitate by filtration. After washing with methyl t-butyl ether (20 mL twice), 4-(5-methoxycarbonyl-1-methylindol-3-ylmethyl)-3-methoxybenzoyl chloride (10.10 g, 90.6%) was obtained as an off-white solid; mp 147°–149° C.; NMR (250 MHz, DMSO-$d_6$): 3.76, 3.92, 3.97 (each s, 3H, NCH$_3$ plus OCH$_3$ plus CO$_2$CH$_3$), 4.16 (s, 2H, ArCH$_2$Ar'), 6.87 (s, 1H), 7.20 (d, 1H), 7.29 (d, 1H), 7.54 (d, 1H), 7.66 (dd, 1H), 7.92 (dd, 1H), 8.32 (d, 1H).

k. 4-(5-Methoxycarbonyl-1-methylindol-3-ylmethyl)-3-methoxy-N-(2-methylphenylsulfonyl)benzamide A solution of 4-(dimethylamino)pyridine (8.17 g, 66.9 mmole) in dichloromethane (20 mL) was added over 15 minutes to a stirred suspension of the product of Example 3.j., above, (9.94 g, 26.8 mmole) and 2-methylbenzenesulfonamide (6.87 g, 40.1 mmole) in dichloromethane (30 mL). After 45 minutes the solution was heated to reflux and 20 mL of distillate collected. Acetone (150 mL) was added and a further 80 mL of distillate collected. The mixture was allowed to cool overnight and finally stirred at 15° C. before collection of the solid by filtration. This was then slurry-washed with methanol (3 times 30 mL) to afford 16.22 g (96.4%) of 4-(5-methoxycarbonyl-1-methylindol-3-ylmethyl)-3-methoxy-N-(2-methylphenylsulfonyl)benzamide as its 4-(dimethylamino)pyridine salt; mp 185°–187° C. (with partial melting and resolidification at 138°–140° C.); NMR (250 MHz, DMSO-$d_6$): 2.53 (s, 3H, ArCH$_3$), 3.13 (s, 6H, N(CH$_3$)$_2$), 3.76, 3.83, 3.86 (each s, 3H, OCH$_3$ plus NCH$_3$ plus CO$_2$CH$_3$), 4.02 (s, 2H, ArCH$_2$Ar'), 6.92 (d, 2H), 7.02 (d, 1H), 7.11–7.32 (m, 4H), 7.39–7.53 (m, 3H), 7.75 (dd, 1H), 7.88 (d, 1H), 8.20 (m, 3H).

l. 4-(5-Carboxy-1-methylindol-3-ylmethyl)-3-methoxy-N-(2-methylphenylsulfonyl)benzamide A mixture of the product of Example 3.k., above, (15 g, 23.8 mmole), concentrated sodium hydroxide liquor (6.75 mL, 119 mmole), water (85 mL) and tetrahydrofuran (18 mL) was stirred for three hours at 65° C., and the now homogeneous solution cooled to 50°–55° C. and maintained at this temperature during the subsequent acidification and extraction. Concentrated hydrochloric acid was added to a pH of 7–8, followed by addition of tetrahydrofuran (44 mL) and n-butyl acetate (29 mL), and further adjustment of the pH to 1–2. The reaction mixture was allowed to settle and the lower aqueous layer separated. The organic layer was washed with 5% brine solution (20 mL twice). The tetrahydrofuran was removed by distillation (about 40 mL distillate collected at a jacket temperature of 95° C.), and the residual mixture cooled to 15°–20° C. The product was collected by filtration, washed with butyl acetate (15 mL) and dried at 50° C. to give 4-(5-carboxy-1-methylindol-3-ylmethyl)-3-methoxy-N-(2-methylphenylsulfonyl)benzamide (11.08 g, 94%); mp 264°–267° C.; NMR (250 MHz, DMSO-$d_6$): 2.63 (s, 3H, ArCH$_3$), 3.78 (s, 3H, NCH$_3$), 3.95 (s, 3H, OCH$_3$), 4.08 (s, 2H, ArCH$_2$Ar'), 7.18 (d, 1H), 7.22 (s, 1H), 7.38–7.65 (m, 6H), 7.79 (d, 1H), 8.06 (d, 1H), 8.20 (s, 1H).

An alternative preparation of (R)-2-methyl-4,4,4-trifluorobutylamine hydrochloride is as follows:

m. Ethyl (E)-2-methyl-4,4,4-trifluorobut-2-enoate

A suspension of (carbethoxyethylidene)triphenylphosphorane (400 g, 1.10 mole) in tetrahydrofuran (600 mL) was treated with aqueous fluoral hydrate (71.5% w/w, 180 g, 1.10 mole) over a period of 4 hours. During the addition the reaction temperature rose to 45° C. and all of the solid dissolved to give a clear brown solution. The mixture was allowed to stand for 15 hours and was then heated under reflux for 3.5 hours. The solution was distilled at 2,700 Pa until the temperature in the distillation flask reached 140° C., giving ethyl (E)-2-methyl-4,4,4-trifluorobut-2-enoate as a solution in tetrahydrofuran (Solution A, 0.75 L, containing a maximum of 201 g of alkene); NMR (270 MHz, CDCl$_3$): 1.3 (t, 3H, J=7Hz), 2.1 (br, s, 3H), 4.3 (q, 2H, J=7Hz) and 6.7 (m, 1H), (plus signals due to tetrahydrofuran).

n. Ethyl 2-methyl-4,4,4-trifluorobutanoate

Solution A from Example 3.m., above, (0.75 L) was treated with 10% (w/w) palladium on carbon (20 g, 50% water wet paste), and the resulting mixture was hydrogenated under a pressure of 2 bar. The reaction was complete after an uptake of hydrogen of 25.9 L. The catalyst was removed by filtration through kieselguhr to give ethyl 2-methyl-4,4,4-trifluorobutanoate as a solution in tetrahydrofuran (Solution B, about 1 L, containing about 200 g of ester) which was used directly in the next stage.

o. 2-Methyl-4,4,4-trifluorobutanoic acid

Solution B from Example 3.m., above, (about 1 L) was treated sequentially with water (500 mL) and lithium hydroxide monohydrate (150 g, 3.6 mole) and was then heated under reflux (70° C.) for 2 hours. The mixture was allowed to cool to room temperature, and the tetrahydrofuran was removed by distillation at 2700 Pa. The resulting aqueous slurry was treated with concentrated hydrochloric acid to pH 2, by which point all solid had dissolved and an oil had separated. The mixture was allowed to stand for 4 days; then the aqueous layer was decanted and extracted with ether (200 mL twice). The separated oil was partitioned between water (500 mL) and ether (500 mL), and the combined ether extracts were dried (MgSO$_4$) and evaporated at room temperature to give the crude acid (171.5 g). Distillation of a 45 g sample of crude acid gave 2-methyl-4,4,4-trifluorobutanoic acid (23.7 g) as a colourless oil; bp 173°–176° C., which was about 95% pure by GLC analysis; NMR (270 MHz, CDCl$_3$): 1.35 (d, 3H, J=7 Hz), 2.05–2.30 (m, 1H), 2.55–2.95 (m, 2H) and 10.2–11.1 (br s, 1H).

p. (RS)-4,4,4-Trifluoro-2-methyl-N-[(S)-1-phenylethyl]butyramide

A solution of 2-methyl-4,4,4-trifluorobutanoic acid (10.0 g, 0.064 mole) in dichloromethane (150 mL) was treated with 4-(N,N-dimethylamino)-pyridine (7.8 g, 0.064 mole), and the mixture was stirred for 15 min. A solution containing (S)-1-phenylethylamine (7.8 g, 0.064 mole) in dichloromethane (50 mL) was added, the mixture was stirred for a further 15 min, and then a solution of dicyclohexylcarbodiimide (15.9 g, 0.077 mole) in dichloromethane (100 mL) was added. Stirring was continued for 15 hours, then the precipitated dicyclohexylurea was removed by filtration, and the filtrate was concentrated to an oil under reduced pressure. The oil was partitioned between 2N hydrochloric acid (100 mL) and ether (100 mL), and the two phase mixture was filtered to remove a further quantity of dicyclohexylurea. The layers were separated; and the ether fraction was washed with 2N hydrochloric acid (100 mL), 2N aqueous sodium hydroxide solution (100 mL) and saturated brine (100 mL); dried (MgSO$_4$); and evaporated to an oil, which solidified on standing. The solid, which comprised a mixture of the two diastereomeric butyramides was used directly in the next step.

q. (R)-4,4,4-Trifluoro-2-methyl-N-[(S)-1-phenylethyl]butyramide

The product of Example 3.p., above, was dissolved in warm toluene (180 mL) and petroleum ether (bp 100°–120° C.) (180 mL) was added. The mixture was stirred at room temperature for 15 hours during which time crystallisation occurred. The white crystalline solid was filtered, washed with petroleum ether (bp 100°–120° C.) and dried at 60° C. to give impure (R)-4,4,4-trifluoro-2-methyl-N-[(S)-1-phenylethyl]butyramide (4.07 g), contaminated with about 3% of the other, unwanted diastereomer, as estimated by HPLC analysis (Spherisob S50DS2 reversed phase column, acetonitrile:water:trifluoroacetic acid:triethylamine (100:100:1:1), FR=1.5 mL/min, UV detector at 260 nm).

The mother liquors from crystallization, which were enriched in the unwanted (S)-4,4,4-trifluoro-2-methyl-N-[(S)-1-phenylethyl]butyramide diastereomer, were recycled as follows:

The mother liquors from the above crystallization (containing about 14.0 g of amide mixture) were evaporated to give an oil, which was redissolved in tetrahydrofuran (150 mL) and treated with potassium tert-butoxide (12.1 g, 2 molar equivalents). The colourless solution became yellow and a slight exotherm was noted. The mixture was stirred for 1 hour, by which time complete equilibration of the diastereomers had occurred, as monitored by HPLC analysis. Water (100 mL) was added, the mixture was stirred for 10 min, then extracted with ether (100 mL twice). The combined ether extracts were washed with water (100 mL twice) and saturated brine (100 mL) then evaporated to an oil. The oil was dissolved in toluene (130 mL) and petroleum ether (bp 100°–120° C.) (130 mL) was added. The solution was seeded with the desired (R,S)-diastereomeric butyramide and stirred at room temperature for 15 hours. The white crystalline precipitate was filtered, washed with petroleum ether (bp 100°–120° C.) and dried at 60° C. to give crude (R)-4,4,4-trifluoro-2-methyl-N-[(S)-1-phenylethyl]-butyramide (0.99 g), contaminated with about 4.0% of the unwanted (S,S)-diastereomer by HPLC analysis.

The combined crude (R)-4,4,4-trifluoro-2-methyl-N-[(S)-1-phenylethyl]butyramide was recrystallised from petroleum ether (bp 100°–120° C.) to give material containing less than 1.0% of the unwanted (S,S)-diastereomer, in about 95% recovery; NMR (270 MHz, CDCl$_3$): 1.2 (d, 3H, J=7 Hz), 1.5 (d, 3H, J=7 Hz), 2.0–2.3 (m, 1H), 2.4–2.6 (m, 1H), 2.6–2.9 (m, 1H), 5.0–5.3 (m, 1H), 5.6–5.9 (br, 1H, s) and 7.2–7.5 (m, 5H).

r. [(R)-2-Methyl-4,4,4-trifluorobutyl][(S)-1-phenylethyl]amine

A solution of borane-tetrahydrofuran complex in tetrahydrofuran (1.0M, 35 mL, 0.035 mole) was cooled to less than 5° C. under a nitrogen atmosphere, and a solution of the product of Example 3.q., above, (3.5 g, 0.0135 mole) in tetrahydrofuran (17.5 mL) was added dropwise over 20 min, maintaining the temperature below 5° C. throughout. The mixture was then heated to reflux for 3 hours. The mixture was cooled to room temperature and a solution of concentrated hydrochloric acid (5.25 mL) in water (20 mL) was added. The mixture was heated to reflux for 30 min, then cooled to room temperature and evaporated to give a damp white solid. The solid was suspended in water (100 mL) and concentrated sodium hydroxide liquor was added to pH 12. The mixture was extracted with ether (3 times 75 mL); and the combined organic extracts were dried (MgSO$_4$) and evaporated to give [(R)-2-methyl-4,4,4-trifluorobutyl][(S)-1-phenylethyl]amine (3.21 g) as a waxy solid; NMR (270 MHz, CDCl$_3$): 1.05 (d, 3H, J=7 Hz), 1.35 (d, 3H, J=7 Hz), 1.5–2.6 (m, 5H), 3.6–3.8 (m, 1H) and 7.2–7.5 (m, 5H).

s. (R)-2-Methyl-4,4,4-trifluorobutylamine hydrochloride

A solution of the product Example 3.r., above, (3.21 g, 0.013 mole) in industrial methylated spirit (5% methanol, 95% ethanol) (100 mL) was treated with 10% (w/w) palladium on carbon (50% water wet paste, 400 mg), and the resulting mixture was hydrogenolysed at 65° C. under a pressure of 3 bar for 3 hours. The mixture was filtered through diatomaceous earth to remove catalyst, concentrated hydrochloric acid (7.5 mL) was added, and the mixture was evaporated. The residue was dried by azeotropic distillation with toluene (75 mL twice), giving a tan coloured solid (2.07 g). A sample of the solid (1.75 g) was recrystallised from dichloromethane (13 mL) and ether (13 mL) to give (R)-2-methyl-4,4,4-trifluorobutylamine hydrochloride (1.21 g) as a white solid, mp 223°–225° C.; $^{19}$F NMR (500 MHz proton decoupled, CFCl$_3$ as reference, 1 mg of (R)-2-methyl-4,4,4-trifluorobutylamine hydrochloride and 50 mg of (R)-(−)-2,2,2-trifluoro-1-(9-anthryl)ethanol in CDCl$_3$): −63.86 (s) ppm. NMR shows presence of 3.6% of the (S)-enantiomer at −63.83 (s) ppm.

EXAMPLE 4

The following illustrates representative pharmaceutical dosages forms which may be used for the therapeutic or prophylactic administration of a compound of formula I or of a pharmaceutically acceptable salt thereof (hereinafter referred to as 'Compound X'):

| (i) Tablet 1 | mg/tablet |
|---|---|
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Compound X' | 20.0 |
| Microcrystalline cellulose | 410.0 |
| Starch | 50.0 |
| Sodium starch glycolate | 15.0 |
| Magnesium stearate | 5.0 |

|  |  | 500.0 |
|---|---|---|
| (iii) | Capsule | mg/capsule |
|  | 'Compound X' | 10.0 |
|  | Colloidal silicon dioxide | 1.5 |
|  | Lactose | 465.5 |
|  | Pregelatinized starch | 120.0 |
|  | Magnesium stearate | 3.0 |
|  |  | 600.0 |
| (iv) | Injection 1 (1 mg/mL) | mg/mL |
|  | 'Compound X' (free acid form) | 1.0 |
|  | Dibasic sodium phosphate | 12.0 |
|  | Monobasic sodium phosphate | 0.7 |
|  | Sodium chloride | 4.5 |
|  | 1.0 N Sodium hydroxide solution (pH adjustment to 7.0–7.5) | q.s. |
|  | Water for injection | q.s. ad 1 mL |
| (v) | Injection 2 (10 mg/mL) | mg/mL |
|  | 'Compound X' (free acid form) | 10.0 |
|  | Monobasic sodium phosphate | 0.3 |
|  | Dibasic sodium phosphate | 1.1 |
|  | Polyethylene glycol 400 | 200.0 |
|  | 0.1 N Sodium hydroxide solution (pH adjustment to 7.0–7.5) | q.s. |
|  | Water for injection | q.s. ad 1 mL |
| (vi) | Aerosol | mg/can |
|  | 'Compound X' | 20.0 |
|  | Oleic acid | 10.0 |
|  | Trichloromonofluoromethane | 5,000.0 |
|  | Dichlorodifluoromethane | 10,000.0 |
|  | Dichlorotetrafluoroethane | 5,000.0 |

It will be appreciated that the above pharmaceutical compositions may be varied according to well-known pharmaceutical techniques to accomodate differing amounts and types of active ingredient 'Compound X'. The aerosol (vi) may be used in conjunction with a standard, metered dose aerosol dispenser.

Formulae

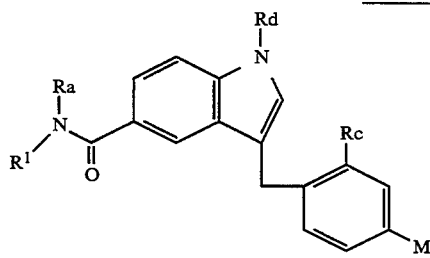

Ia

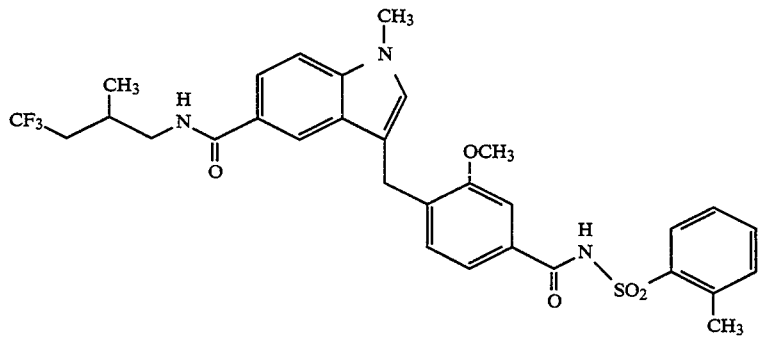

I

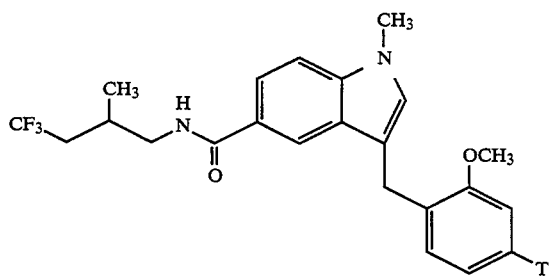

II

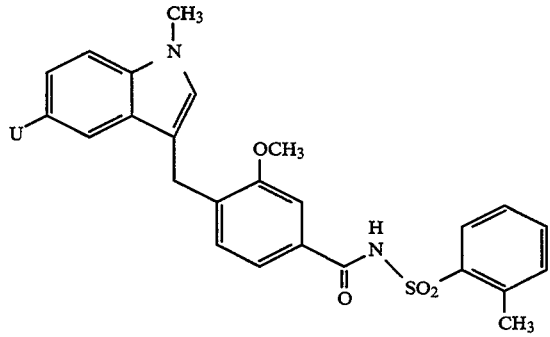

III

Formulae
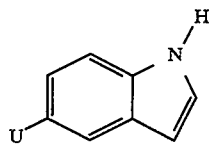
IV
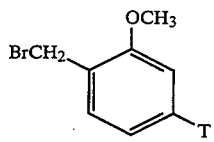
V
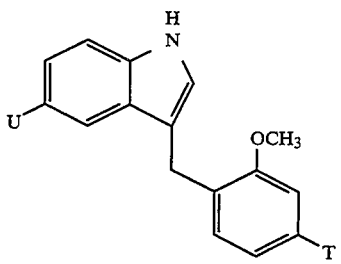
VI
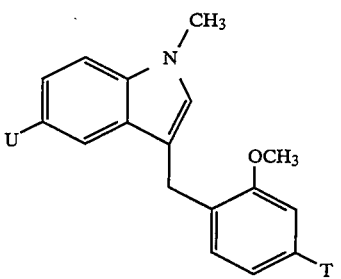
VII
What is claimed is:
1. 2-Methyl-4,4,4-trifluorobutylamine, or an acid solution salt thereof.
2. A compound as claimed in claim 1 which is of the substantially pure (R)-form.
* * * * *

UNITED STATES PATENT AND TRADEMARK OFFICE
CERTIFICATE OF CORRECTION

PATENT NO. : 5,334,765
DATED : August 2, 1994
INVENTOR(S) : Robert T. Jacobs

It is certified that error appears in the above-identified patent and that said Letters Patent is hereby corrected as shown below:

Column 1, line 56, "solyates" should read --solvates--

Column 3, line 43, "4-dimethylamimopyridine)" should read --4-dimethylaminopyridine)--

Column 8, line 1, "Am Hg)" should read --mm Hg)--

Column 9, line 61, "3-metboxybenzoate" should read --3-methoxybenzoate--

Column 13, line 5, "for for" should read --for--

Column 16, line 3, "rook" should read --room--

Column 19, line 38, "AR$\underline{CH}_3$)" should read --Ar$\underline{CH}_3$--

Column 21, line 51, "N($CH_3$)2)" should read --N($CH_3$)$_2$)--

UNITED STATES PATENT AND TRADEMARK OFFICE
CERTIFICATE OF CORRECTION

PATENT NO. : 5,334,765

DATED : August 2, 1994

INVENTOR(S) : Robert T. Jacobs

It is certified that error appears in the above-indentified patent and that said Letters Patent is hereby corrected as shown below:

Column 27, line 38, "acid solution" should read --acid addition--.

Signed and Sealed this

Ninth Day of May, 1995

Attest:

BRUCE LEHMAN

Attesting Officer

Commissioner of Patents and Trademarks